United States Patent
Lewington et al.

(10) Patent No.: US 8,138,909 B2
(45) Date of Patent: Mar. 20, 2012

(54) PORTABLE DETECTION SYSTEM AND METHOD

(75) Inventors: Jay Lewington, Surrey (GB); John Walter Czajka, West Grove, PA (US); Douglas Jason Green, Baldwin, MD (US); Carmelo Volpe, Hertfortshire (GB)

(73) Assignees: Smiths Detection Inc., Edgewood, MD (US); Smiths Detection—Watford Limited, Hertfordshire (GB)

( * ) Notice: Subject to any disclaimer, the term of this patent is extended or adjusted under 35 U.S.C. 154(b) by 660 days.

(21) Appl. No.: 12/216,312

(22) Filed: Jul. 2, 2008

(65) Prior Publication Data

US 2009/0066507 A1  Mar. 12, 2009

Related U.S. Application Data

(60) Provisional application No. 60/929,577, filed on Jul. 3, 2007.

(51) Int. Cl.
*G08B 29/00* (2006.01)

(52) U.S. Cl. .... 340/514; 340/588; 340/629; 340/539.26

(58) Field of Classification Search .................. 340/514, 340/538.15, 539.17, 539.1, 539.13, 579, 340/539.26, 552, 585–586, 588, 601–602, 340/617, 629
See application file for complete search history.

(56) References Cited

U.S. PATENT DOCUMENTS

| | | | | |
|---|---|---|---|---|
| 5,108,889 A | * | 4/1992 | Smith et al. | 435/4 |
| 6,649,358 B1 | * | 11/2003 | Parce et al. | 435/7.2 |
| 6,931,326 B1 | * | 8/2005 | Judson et al. | 702/20 |
| 6,982,431 B2 | * | 1/2006 | Modlin et al. | 250/573 |
| 7,329,738 B1 | * | 2/2008 | Lee et al. | 530/391.1 |
| 2002/0177135 A1 | | 11/2002 | Doung et al. | |
| 2003/0153021 A1 | * | 8/2003 | Lu et al. | 435/7.32 |
| 2004/0082332 A1 | | 4/2004 | McCann et al. | |
| 2005/0069454 A1 | | 3/2005 | Bell | |
| 2007/0031283 A1 | * | 2/2007 | Davis et al. | 422/58 |

FOREIGN PATENT DOCUMENTS

| | | |
|---|---|---|
| GB | 2 365 122 | 2/2002 |
| WO | WO 98/24548 | 6/1998 |
| WO | WO 00/52444 A2 | 9/2000 |
| WO | WO 02/061417 A2 | 8/2002 |
| WO | WO 03/082425 A2 | 10/2003 |

(Continued)

OTHER PUBLICATIONS

International Search Report and Written Opinion dated Dec. 18, 2008, received in corresponding International Application No. PCT/US2008/069022 (17 pgs.).

(Continued)

*Primary Examiner* — Daniel Previl
(74) *Attorney, Agent, or Firm* — Casimir Jones, S.C.

(57) ABSTRACT

A method and apparatus for providing assay information to a portable detection unit, by way of a remote server in communication with the portable detection unit or a consumable with stored information for use with the portable detection unit. Global Positioning System (GPS) information is provided to a portable detection unit having a GPS receiver, so that the unit can determine its current position, including altitude. Based on the determined position, assays and parameters, such as PCR melt temperatures, can be selected. Assays to be performed by the portable detection unit can be selected based on the results of a prior assay.

21 Claims, 3 Drawing Sheets

FOREIGN PATENT DOCUMENTS

| | | |
|---|---|---|
| WO | WO 2005/019836 A2 | 3/2005 |
| WO | WO 2005/024437 A1 | 3/2005 |
| WO | WO 2006/013573 A2 | 2/2006 |
| WO | WO 2007/083130 A1 | 7/2007 |

OTHER PUBLICATIONS

International Preliminary Report on Patentability for PCT/GB2007/000164 (6 pgs.), to Enigma Diagnostics Limited.

* cited by examiner

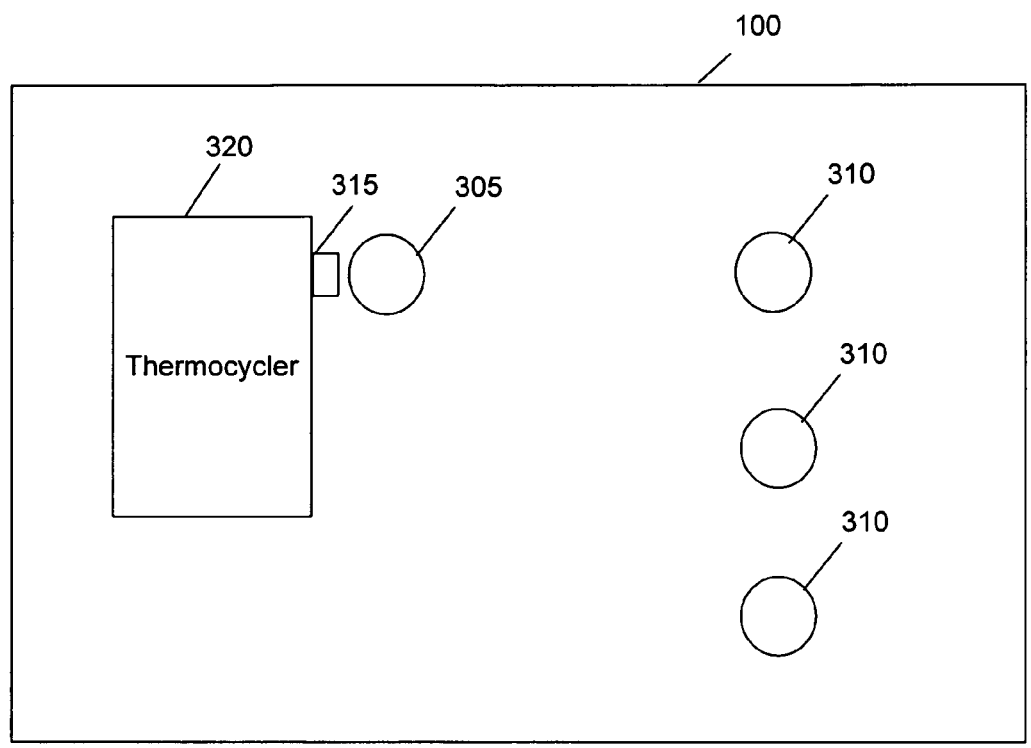
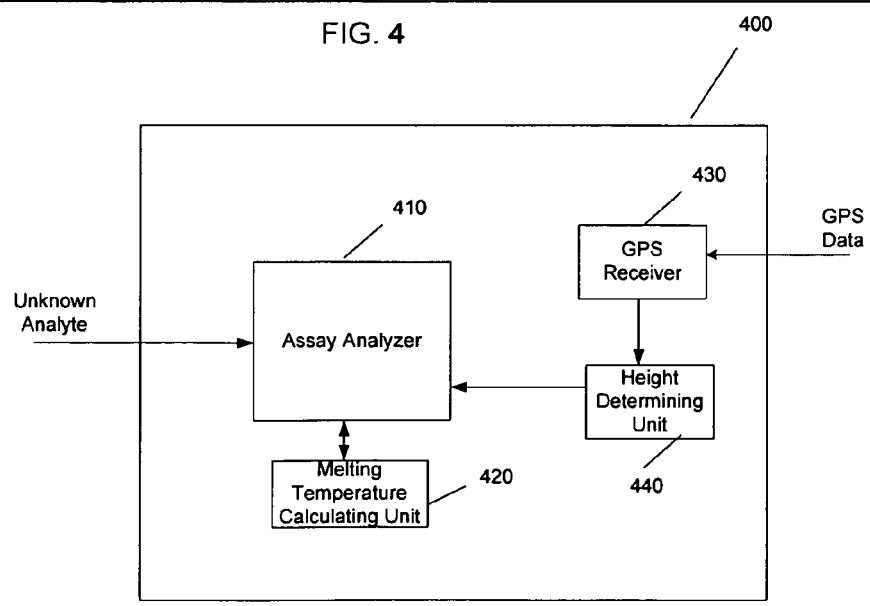

PORTABLE DETECTION SYSTEM AND METHOD

This application claims benefit to U.S. provisional patent application No. 60/929,577, filed Jul. 3, 2007 to Lewington et al., which is hereby incorporated by reference in its entirety.

FIELD

This invention is related in general to the field of portable detection systems. More particularly, the invention is related to a method and system for providing a communications capability for a portable detection device so that the portable detection device can receive data from and transmit data to a server, and to enable the portable detection device to determine a position and height to be used in an assay analysis computation. The ability to send and receive data also can be used, for example, to determine what type of analysis to be performed or the parameters to be used to perform the analysis. The results can be transmitted to a server.

BACKGROUND

Portable detection units are becoming very useful in today's society, with the threat of terrorism being more and more prominent. In more detail, bioterrorism and biological warfare pose both physical and psychological threats to military and civilian forces, as well as to civilian populations.

The difficulty and time needed to identify potentially dangerous biological or chemical agents exacerbates the risks and fear associated with biological warfare. For example, potential threats may be an unknown liquid left at a subway station or an unknown gas emanating from a building. Because of the time needed to assess potential threats, first responders are left with a choice. People can be permitted to continue traveling and risk further spreading the biological agents, or the area can be isolated causing potentially large disruptions and expense for what may be nothing more than spilled coffee creamer.

In an effort to more quickly identify biological agents and respond to attacks, efforts have been made to develop portable detection units, such as portable Polymerase Chain Reaction (PCR) units. However, these portable units often can only be used by highly trained personnel making field use difficult. Thus, a need exists for a portable detection unit that can be used easily and effectively by field personnel with little training.

SUMMARY

An aspect of the present invention relates to a method and apparatus for providing updating assay information to a portable detection unit, by way of a remote server. The remote server can also provide corrected annealing temperatures for strain differentiating assays to the portable detection unit.

Another aspect of the invention relates to a consumable for use with a portable detection unit. The consumable has a memory unit that can provide information to the portable detection unit. The information can include what detection protocol should be used, the assay parameters, or the detection parameters, for example. The consumable may also have a communications unit, such as a microprocessor. This communications unit can send information from the memory unit to the portable detection unit or a remote server or receive information, such as from the portable detection unit or remote server. For example, the communications unit may receive data from a remove server and then communicate this data to the portable detection unit.

A consumable can also be labeled with an identification device, such as, for example, a barcode, for use with a portable detection unit. The identification device can provide information to the portable detection unit. For example, the identification device can specify assay parameters are used, including assay temperatures, timing, and detection parameters. The identification device can also simply identify the reagents or the quantity of reagents, so the portable detection unit can make the appropriate analysis or properly analyze results. The identification device can be used in place of the memory unit or in addition to the memory unit. For example, a consumable can contain an identification device to identify the type of detection protocol and a memory unit containing the detection protocol parameters. Any type of barcode, including linear barcodes, matrix barcodes (otherwise known as 2D barcodes), and stacked barcodes, can be used. The identification device also may contain assay parameters including assay temperatures, timing, and detection parameters.

Another aspect of the present invention relates to maintaining cycling data specific to a reaction on a consumable by a remote server and transmitting the cycling data to a portable detection unit.

Yet another aspect of the present invention relates to providing Global Positioning System (GPS) information to a portable detection unit, so that the unit can determine its current altitude and adjust a melt temperature used during a PCR procedure performed of an unknown substance, so as to avoid boiling, for example, during a denaturation phase of the PCR procedure. The assay parameters, such as temperature, timing, and detection parameters can be selected based on the geographic location of the portable detection system as determined by the GPS. For example, a first set of assay parameters can be used in the United States and a second set of assay parameters can be used in Europe. It may be desirable to select different detection protocols or parameters based on the laws and regulations that differ by geographic region.

In accordance with one aspect of the invention, there is provided a system for testing an unknown sample, which includes a portable detection unit having stored therein assay parameter information for testing the unknown sample with respect to a plurality of assays. The system also includes a remote server providing updated assay parameter information to the portable detection unit.

In accordance with another aspect of the invention, there is provided a system for testing an unknown sample, which includes a portable detection unit that stores cycling data specific to a reaction on a consumable. The system also includes a remote server providing updated cycling data to the portable detection unit.

In accordance with yet another aspect of the invention, there is provided a portable detection unit for testing an unknown sample. The unit includes a memory having stored therein assay parameter information for testing the unknown sample with respect to a plurality of assays, the assay parameter information including a minimum melt temperature for each of the plurality of assays. The unit can also include a height determining unit configured to determine a current height of the portable detection unit with respect to sea level. The unit can further include a melting temperature recalculating unit configured to recalculate the melt temperature for the plurality of assays based on the current height of the portable detection unit.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and, together with the description, serve to explain the principles of the invention.

FIG. 3 is a diagram showing a portable detection unit tray according to at least the first embodiment of the invention.

FIG. 4 is a block diagram showing a system for determining a correct melt temperature based on a current position of a portable detection unit, according to yet another embodiment of the invention.

DETAILED DESCRIPTION

Reference will now be made in detail to embodiments of the invention, examples of which are illustrated in the accompanying drawings. An effort has been made to use the same reference numbers throughout the drawings to refer to the same or like parts.

Unless explicitly stated otherwise, "and" can mean "or," and "or" can mean "and." For example, if a feature is described as having A, B, or C, the feature can have A, B, and C, or any combination of A, B, and C. Similarly, if a feature is described as having A, B, and C, the feature can have only one or two of A, B, or C.

Unless explicitly stated otherwise, "a" and "an" can mean "one or more than one." For example, if a device is described as having a feature X, the device may have one or more of feature X.

Figure 1:
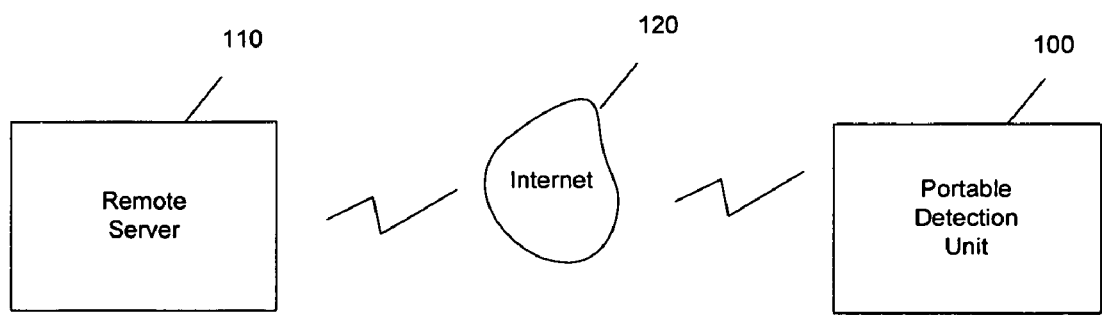
FIG. 1 is a diagram showing a system for updating assay parameter information of a portable detection unit, according to a first embodiment of the invention.

FIG. 1 shows a portable detection unit 100 in communication with a remote server 110, according to a first embodiment of the invention. Any portable detection unit can be used. In some embodiments, the portable detection unit can be designed to perform PCR analysis. The portable detection can also be designed to perform some other type of analysis, such as ion mobility spectrometry (IMS), mass spectrometry, or affinity-based analysis. Examples of affinity-based analysis include protein affinity analyses, such as analysis of antibody binding or use of protein arrays. The portable detection units perform more than one type of analysis. For example, the portable detection device may evaluate analyte based on size followed by some other type of analysis, such as PCR, mass spectrometry, or affinity-based analysis depending on the type and size of the analyte. In one embodiment, the portable detection unit first determines the size of the analyte, such as by using mass spectrometry, followed by PCR, if the analyte meets threshold criteria.

In some embodiments, the portable detection unit 100 may correspond to a Bioseeq™ unit (Smiths Detection Inc.), such as, for example a Bioseeq Plus™ unit. The portable detection unit 100 may alternatively correspond to an enhanced Bioseeq™ unit, with those enhancements to be described hereinbelow in detail. In either the enhanced Bioseeq™ unit or the Bioseeq Plus™ unit, a user (or operator) does not need to perform any complex functions in order to analyze a sample; rather, the user need only collect an unknown sample, select a particular assay or assays (on Bioseeq2, for example, the memory chip can contain the details of the assay) to be run by the portable detection unit 100, and then await the results of those assays as provided on a display of the portable detection unit 100.

The portable unit can accommodate multiple simultaneous assays. The number of simultaneous assays will depend on the application and the specific device. For example, the Bioseeq Plus™ unit supports up to six independent simultaneous assays, includes thermocycler heaters for temperature stability, a keyboard for user entry of information, and an internal battery that can be recharged. The assays that are available for use with Bioseeq Plus™ unit include, for example, a) Anthrax, b) Tularemia, 3) Plague, 4) Orthopox, 5) Ricin, and 6) Training consumables. Other assays can be used depending on the desired use. The assays protocols are stored within a memory of the Bioseeq Plus™ unit. Again, although a Bioseeq™ unit may be used as the portable detection unit, other types of portable detection devices can be also be used.

While the Bioseeq™ unit can be used as the portable detection unit, any portable detection unit can be used. The portable detection unit can be designed to perform PCR analysis. The portable detection can also be designed to perform some other type of analysis. In some embodiments, the portable detection units perform more than one type of analysis. For example, the portable detection device may evaluate analyte based on size followed by either PCR or mass spectrometry or affinity-based analysis depending on the type and size of the analyte.

In the first embodiment, the communication between the portable detection unit 100 and the remote server 110 is made by way of a wireless communication link, whereby that wireless communications link may provide a link to the remote server 110 via the Internet 120, or the link may provide a direct link to the remote server 110. The portable detection unit 100 and the remote server 110 can communicate via a satellite or one or more intermediary devices, such as workstations. The intermediary device can be set up at a site remote from the site of both the portable detection unit 100 and the remote server 110. For example, portable detection unit 100 may be used at the site of a potential bioterrorist attack and communicate, such as by a wireless communications link, with workstations located at a command site outside the area of potential contamination. These workstations can then communicate with the remote server 110 to send information to or from the portable detection unit 100.

The information received by the portable detection unit 100 can be the information used to analyze the sample. For example, the remote server 110 can specify the types of assays to perform. In some embodiments, the remote server 110 can communicate with the portable detection unit 110 to instruct the portable detection unit 100 to perform a particular PCR assay, such as an assay for anthrax. In some embodiments, the portable detection unit 100 can communicate the results of the assay to the portable detection unit 110. Based on this information, the remote server 110 can send instructions for performing additional assays or modifying the prior assay in some manner. For example, if the results of the first assay are negative, additional assays to be performed. In this manner, the remote server 110 can send instructions to perform the assays necessary to identify the sample or rule out that the sample contains a particular agent.

The remote server 110 can also specify the conditions under which assays can be performed by the portable detection unit 100. The conditions can include, for example, the types and amounts of reagents, the reactions to be performed, the timing of each of the steps, the temperatures that should be maintained, and the detection parameters. In some embodiments, the assay is a PCR assay, and the remote server 110 provides the portable detection unit 100 with the reagents to use, the number of cycles, the time of each cycle, the temperature for each cycle, temperature profiles, detection temperatures, or detection excitation and emission wavelengths.

By providing information to the portable detection unit 100, the portable detection unit 100 can be operated by personnel with very limited training. In one embodiment, the portable detection unit 100 is a Bioseeq Plus™ unit. The remote server 110 can provide information to the Bioseeq Plus™ unit to specify what assays to perform and the conditions that should be used to perform the assays. In some embodiments, the user does not need to provide any input to the Bioseeq™ other than the sample to be tested.

In the first embodiment, assay parameters are provided to the portable detection unit 100 from the remote server 110 (that is, remotely located with respect to the portable detection unit 100) via the wireless communications link, so that a user of the portable detection unit 100 has the latest information downloaded to the portable detection unit 100 in order to analyze gases, liquids and/or solids by way of the portable detection unit 100. Not shown in FIG. 1 is a memory provided in the portable detection unit 100, for storing assay parameters and for storing program code for performing PCR steps on unknown samples that have been collected for analysis by the portable detection unit 100.

The remote server 110 is provided with a link, preferably a secure link (e.g., using encryption and decryption algorithms), to a central facility, such as a medical research facility, so that updated assay information is provided to the remote server 110 periodically from the medical research facility, whereby that information can be downloaded to the portable detection unit 100 when needed. The remote server 110 can receive information at fixed intervals, such as hourly, once per day, or once per week. The remote server 110 can also receive information on demand, such as when the remote server receives information that a portable detection unit is activated or when it is about to perform an assay.

In the first embodiment, when a user turns on his/her portable detection unit 100, the portable detection unit 100 outputs an "awake" signal, which may be a radio frequency (RF) signal that is received by a local communications system (e.g., cellular, satellite or WI-FI system). The remote server 110 is notified of this awakening by the awake signal being provided to it over-the-air and/or via the Internet from the local communications system. The remote server 110 then checks its latest assay information with the assay information that was previously sent to the portable detection unit 100 the last time the portable detection unit 100 was awakened, and an update of assay information is automatically provided to the portable detection unit 100 from the remote server 110 if needed. Alternatively, the updated assay information is provided to the portable detection unit 100 only when a consumable (e.g., a canister containing the consumable) is placed into a particular bay of the portable detection unit 100, to initiate the running of an assay on a collected sample.

By way of example, assume that the portable detection unit 100 is being used to check flu viruses of patients at a hospital. A flu differentiating assay containing the parameters for detecting the latest threat virus would be stored at the remote server 110, and then downloaded to the portable detection unit 100, along with the correct annealing temperatures for performing the strain differentiating assay or assays. Once the updated information has been downloaded to the portable detection unit 100, a notification is made (e.g. via a message on a display of the portable detection unit 100, and/or via an audible beep, or both), to notify the user that he/she can begin to test patients for a potentially deadly new flu virus. This updating of assay parameter data stored in the portable detection unit 100 is performed without changing the chemistry in the stockpiled consumables of the portable detection unit 100. The stockpiled consumables correspond to reagents that are stored (e.g., in canisters) for use by the portable detection unit 100 in performs various assays (e.g., consumable A is used as a reagent to perform an assay to determine if a collected sample is anthrax, and consumable B is used to perform an assay to determine if a collected sample is plague).

In one possible implementation, the portable detection unit 100 is housed on a tray, on which a plurality (e.g., three or more) of canisters containing consumables for performing particular assays are housed. In order to run a particular assay requiring a particular consumable, the canister for that particular consumable is placed on a particular bay of the tray, to initiate running of that particular assay. If a canister containing a particular consumable is empty (whereby that indication can be made via a message on the display of the portable detection unit 100, for example), the user has to remove the empty canister from the bay and insert a new canister containing that same consumable, in order to be able to perform a particular assay requiring that particular consumable as a reagent.

In a second embodiment, a consumable contains information to be supplied to the portable detection unit 100. The information can be stored on the consumable using a memory unit, identification device, or any other suitable information storage tool. The identification device can be, for example, a barcode or RF ID. The information can be communicated to the portable detection unit 100 or the remote server 110 or information can be received from the portable detection unit 100 or the remote server 110 and stored on the memory, as described in greater detail below.

The consumable can contain the different reagents needed to perform an assay or the probes used to detect analyte. For example, the consumable can be a PCR consumable that contains the reagents, primers, and probes used to perform a PCR assay. The consumable can be specific for a particular type of assay. For example, the consumable can be a PCR consumable for use in an assay to detect a particular biological agent, such as, for example anthrax, plague, foot and mouth disease virus, avian influenza, swine fever, Barrett's esophagus, MRSA, HIV, HCV, HPV, or tularemia. When a memory unit is used, the memory can be attached to the consumable in any manner (e.g., on an outer surface of a canister in which consumable is provided). For example, the memory can be embedded in the consumable or attached to the consumable using an adhesive, for example. The memory can be provided in the form of an electronic chip. Similarly, a identification device, such as a barcode can be placed anywhere on the consumable. The only limitation is that the identification device must be capable of being read by the portable detection unit.

The memory can be any form of memory, such as random access memory, flash memory, or any other of memory suitable for storing information. The memory can be in communication with one or more electronic components, such as a microprocessor. For example, the memory can be part of an electronic chip that includes a microprocessor and device for communicating the data stored in the memory to the portable detection unit 100 or remote server 110. In some embodiments, the memory is provided in the form of an radio frequency identification (RF ID) chip. For ease of reference, the terms "memory" and "chip" will be used interchangeably.

The memory can contain information to identify the type of consumable. For example, the memory can identify the consumable as the consumable to be used to identify a particular biological agent, such as plague, anthrax, smallpox, influenza, or tularemia. The memory can also identify the consumable generally, such as by the types of reagents or probes contained within the consumable. Based on this information, the user of the portable detection unit 100 can select specific detection parameters. For example, the consumable can identify itself to the portable detection unit 100 as a PCR consumable for the detection of plague, and the user can then select specific parameters, such as the number of cycles.

The memory can also contain information used to perform an assay. This information can include the type of assay to be performed, the assay parameters, and the detection parameters. For example, the memory can specify the reaction steps, the amounts and types of reagents to be used, and the reaction conditions, such as time and temperature. Thus, the memory can provide all of the information necessary for the portable detection unit 100 to perform an assay and detect sample. In some embodiments, the user can have the option of changing the parameters provided by the memory. This allows sophisticated users to optimize settings, correct settings that have been incorrectly provided by the memory, or perform maintenance.

Information can also be stored on the consumable using a barcode. A barcode can be used to store the same types of information as the memory, as discussed above. In some embodiments, both a barcode and a memory can be used. For example, a barcode can identify the type and quantity of consumable, and the memory can contain testing parameters. A barcode can also be used to corroborate at least a portion of the information on the memory.

In some embodiments, the consumable is a PCR consumable, and the information contained in the memory or identification device contains the information needed for the portable detection unit 100 to perform a PCR assay. The memory can specify, for example, the reagents to use, the number of thermal cycles, the time of each cycle, the temperature for each cycle, temperature profiles, detection temperatures, or detection excitation and emission wavelengths. In some embodiments, the information on the PCR consumable provides all of the information necessary for the portable detection unit 100 to perform an assay such that a user does not need to provide any information. In other embodiments, the information provides only a portion of the necessary parameters, and a user provides additional parameters to the portable detection unit. In further embodiments, all information or supplemental information will be provided by communication of the portable detection device with a remote server.

Because the consumable can provide all, or substantially all, of the information needed to perform an assay to the portable detection unit 100 using the memory or identification device, the consumable allows the portable detection unit to be operated by personnel with very limited training. For example, the portable detection unit 100 could be operated by soldiers or emergency medical personnel with no formal scientific training. Errors are also minimized, because parameters are provided by the consumable rather than users, which may incorrectly enter parameters.

In some embodiments, the consumable with memory can send and receive information from the remote server 110, as described above in relation to the first embodiment, but whereby the portable detection unit 100 is not involved in this information transfer. In those embodiments, only when the consumable is to be utilized to perform a particular assay by the portable detection unit 100 would the information provided by the remote server 110 to the consumable be transferred from the memory of the consumable to the portable detection unit 100 (via a communications unit of the consumable). Thus, the remote server 110 can receive information provided by the memory or provide information to be stored on the consumable's memory. For example, if assay parameters are optimized after the manufacture of a consumable, a wireless communication link can be used to change the parameters stored in the memory of consumables to comport with the optimized parameters. The memory of consumables can also be read to determine the type of consumable. Such reading could be performed using an RF ID communication protocol. This may be useful in inventorying consumables stored in a warehouse, for example.

In some embodiments, the portable detection unit 100 can read the information on the identification device of a consumable an transmit the information to the remote server 110. The remote server 110 can then specify the types of testing or testing parameters to be performed by portable detection unit 100.

In some embodiments, both the consumable and the remote server 110 provide information to the portable detection unit 100. For example, the consumable's memory or identification device can provide the type of consumable and reagents contained, and the remote server 110 can provide the assay and detection parameters. As another example, the consumable's memory or identification device can provide all of the information needed to perform an assay to the portable detection unit, and the remote server 110 can confirm that the information is the most up to date information or update the information, if necessary.

The consumable with memory or a identification device and portable detection unit 100 can be designed to communicate automatically or a user may initiate the exchange of information. For example, once the consumable is loaded into the portable detection unit 100, the portable detection unit 100 can automatically read the information from the consumable. The portable detection unit can also ask the user whether it wishes to use the information stored on the consumable or enter other information.

In one embodiment, the consumable is in the form of a canister and the memory is part of a chip attached to the canister. When the portable detection unit 100 detects the presence of the chip on the canister when the canister is provided within the bay, and when the portable detection unit 100 thereby determines that a particular assay is to be performed using that consumable, updated assay parameter data is provided to the portable detection unit 100, from the remote server 110, without any inputs required from the user. Thus, all the user has to do is to collect the sample, put the consumable into the bay of the portable detection unit 100, and allow the portable detection unit 100 to automatically detect the chip on the consumable in the bay and then to automatically perform an assay using that consumable and the latest assay parameter information. Once that automatic updating has been completed, whereby such an indication may be made via an audible and/or visible indication, the user need only start running a particular assay by making an appropriate selection (e.g., engage a "run ricin test" button, or engage a "run plague test" button, or make a suitable selection on a touch screen display) on the portable detection unit 100. In another possible implementation, the results of an assay, the date and time it was performed, the location where it was performed, and user input date provided for running the assay (e.g., log numbers) are stored on the chip.

In one possible implementation of the first embodiment, the consumable chip is an RF ID chip, whereby its presence at a particular bay within a tray of the portable detection unit 100 is detected, information (e.g., computer software stored in a memory of the RF ID chip) is obtained from the chip, and the portable detection unit 100 performs a particular assay using the information obtained from the chip. Such information may include, for example, cycle time, cycle temperature, temperature profiles, cycle number, detection temperatures, detection excitation parameters, and emission wavelengths. Again, the actual steps of running a particular assay are not described in detail below, as these steps are well-known.

In a third embodiment of the invention, the remote server 110 maintains data specific to a reaction on a consumable. When the portable detection unit 100 is to perform a particular assay, updated data is then provided to the portable detection unit 100 by way of the remote server 110. Updated data can also be provided to the consumable's memory either directly from the remote server 110 or via the portable detection unit 100. That way, product updates are invisible to the user of the portable detection unit 100. Furthermore, any new reaction optimizations can be identified (e.g., by scientists who work at research hospitals) and provided directly the remote server 110, and whereby that information is then downloaded to the portable detection unit 100 or the memory of a consumable, as needed. These downloads can be made based on the manufacture data of the portable detection unit 100, the identity of the assays and the consumables, or the date of manufacture of the consumables. By way of example, when the remote server 110 is provided with updated data for a particular PCR procedure (e.g., the annealing temperature used during cycle two has changed from 93 degrees C. to 95 degrees C., as determined by a scientist performing optimization tests at a laboratory for a particular PCR procedure, whereby that updated information is provided to the remote server 110 via a dedicated communications link between the laboratory and the remote server 110), that information is provided to the portable detection unit 100 via the wireless communications link. Accordingly, all future PCR procedures performed on samples-to-be-tested by using a particular consumable housed within a canister having a chip (e.g., RF ID chip) provided thereon, will utilize the updated cycling data.

Figure 2:
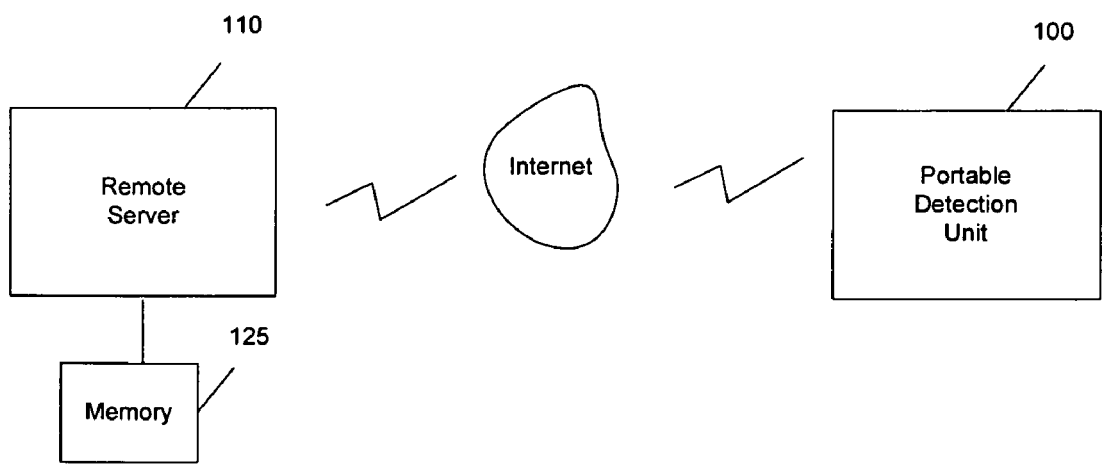
FIG. 2 is a diagram showing a system for updating cycling data information of a portable detection unit, according to another embodiment of the invention.

FIG. 2 shows the remote server 110 having a memory 125 that stores the latest data, and whereby that data is provided to the portable detection unit 110 either when the portable detection unit 100 is turned on (via an "awake" signal output by the portable detection unit 100, as described previously) or when that data has been updated in the memory 125. That way, when the data has been updated in the memory 125 of the remote server 110 after the portable detection unit 110 has been turned on, that event will automatically cause a download of the updated data from the remote server 110 to the portable detection unit 100 (which, since it is turned on, will receive and store that updated cycling data). Alternatively, the data is only be provided to the portable detection unit 100 when a canister containing a particular consumable to be used for running a particular assay is placed into a bay of the portable detection unit 100, whereby the chip on the exterior surface of the canister is then detected, which causes the portable detection unit 100 to send out a signal requesting updated cycling data from the remote server 110. The detection of the canister within the bay may be made via a low-power antenna provided nearby the tray. For example, the low-power antenna may be located 1 inch from the bay, whereby it will only detect signals from an RF ID chip provided on a canister within the bay, and not from RF ID chips provided on other unused canisters provided further away from the antenna on the tray. The remote server 110 then sends, via a wireless signal, the latest cycling data to the portable detection unit 100, which then uses that latest data in performing an assay using the consumable.

FIG. 3 shows the portable detection unit 100 having three storages bays 310, and one usage bay 305. The number of storage bays 310 is based on the number of different consumables (and thus, the number of different canisters) required for running different types of assays by the portable detection unit 100, whereby only three storage bays 310 are shown in FIG. 3 for sake of simplicity. However, the portable detection unit 100 can have any number of storage bays 310. For example, the portable detection unit can have one, two, three, four, five, six, or more storage bays 310. When a particular assay is to be performed using a particular consumable, the canister containing the particular consumable is moved from one of the storage bays 310 to the usage bay 305. An RF antenna 315 can detect an RF ID chip provided on the exterior surface of the canister provided within the usage bay 305, and assay information stored in the chip is then provided to a thermocycler unit 320, for example, of the portable detection unit 100. As explained earlier, prior to the portable detection unit 100 running a particular assay using the particular consumable, it can notify the remote server 110, which then provides updated assay parameter (and/or cycling data) information to the portable detection unit 100. Once that download is complete, the portable detection unit 100 runs the particular assay on a collected sample using the updated information.

A fourth embodiment of the invention will be described below, with reference to FIG. 4. In the fourth embodiment, a portable detection unit 400 includes a global positioning satellite (GPS) receiver, so that the current position of the portable detection unit 400 can be determined. The method of determining a position of a unit based on GPS data is well known in the art, and will not be discussed herein for sake of brevity (e.g., by use of GPS data from at least three different GPS satellites, one can obtain precise position coordinates at any location on the Earth's surface). In the fourth embodiment, the GPS data is utilized by the portable detection unit 400 in order to modify and/or control the assay parameters stored in the portable detection unit 400 or the memory of a consumable.

In more detail, by way of example, even though very high melt temperatures (e.g., 95 degrees C.) are used during a PCR procedure performed by the portable detection unit 400, a minimum melt temperature for an assay would be encoded on a consumable. This encoding may be made via a chip (e.g., RF ID chip) provided on the canister containing the consumable, and may alternatively be made by way of a bar code or other type of permanent or semi-permanent indicia provided on an outer surface of the canister, whereby a scan of that bar code by the portable detection unit 400 will be read and stored by the portable detection unit 400, so that a proper PCR procedure can be performed to obtain enough of the collected sample to perform one or more assays.

In more detail, a PCR procedure involves three steps: a denaturation phase, an annealing phase, and an extension phase. The denaturation phase is a phase whereby DNA fragments of a collected sample are heated at high temperatures, which reduce the DNA double helix to single strands, and whereby these single strands become accessible to primers. The annealing phase is whereby the reaction mixture is cooled down, and primers anneal to the complementary regions in the DNA template strands, and double strands are formed again between primers and complementary sequences. The extension phase is whereby the DNA polymerase synthesizes a complementary strand, whereby an enzyme reads the opposing strand sequence and extends the primers by adding nucleotides in the order in which they can pair. This three-step PCR process is repeated over and over, whereby the cycling of temperatures results in copying of copies, and so on, leading to an exponential increase in the number of copies of specific sequences (that is, an increase in the amount of a sample to be tested). Once an ample amount of sequences is obtained, the portable detection unit 300 can perform an analysis of a sufficient amount of the sample to determine if it poses a threat or not.

Based on the GPS data provided to the portable detection unit 400, the portable detection unit 400 can readily determine its current altitude and thereby modify the melt temperature to avoid boiling. In one possible implementation of the fourth embodiment, the portable detection unit 400 has an internal memory (e.g., Read Only Memory, or ROM) that stores altitude data based on a particular GPS position (latitude and longitude in degrees, minutes and seconds), or a remote server (not shown, but see FIGS. 1 and 2) can provide the precise altitude information to the portable detection unit 400 based on the GPS data being wirelessly communicated to the remote server from the portable detection unit 400. For example, if the portable detection unit 400 is at 10,000 feet altitude, then the temperature to cause a liquid to boil is less than it would be at sea level, whereby the exact boiling temperature based on altitude is known in the art and will not be discussed herein for sake of brevity. Computer program code for calculating the correct boiling temperature based on temperature is stored in a melting temperature calculating unit 420 of the portable detection unit 400 (see FIG. 4).

With reference to FIG. 4, the portable detection unit 400 has a GPS receiver 430 that receives GPS information from GPS satellites, whereby that information is provided to a height determining unit 440. The height determining unit 440 determines the current height of the portable detection unit 400 with respect to sea level. The current height is provided to an assay analyzer 410, which sends that information to a melting temperature calculating unit 420, along with information as to a particular assay, so that a corrected melting temperature based on the current height for the assay can be determined. Based on the corrected melting temperature provided to the assay analyzer 410 by the melting temperature calculating unit 420, the assay analyzer can perform a proper assay (in more detail, the assay analyzer can perform a proper denaturation phase of a PCR procedure by heating DNA fragments of a sample at a temperature that is sufficiently high enough, but not too high to cause boiling to occur).

Based on well known computations relating altitude and boiling temperature, the melt temperature can be readily determined by the portable detection unit 400, no matter its current height (e.g., use on a mountain or underwater). If the minimum melt temperature is determined to be above the calculated boiling point for water at the GPS-determined location of the portable detection unit 400, the portable detection unit 400 will issue a warning message on a display (can also be an audible alert) and prevent the assay from running on the portable detection unit 400. Otherwise, the assay is allowed to run on the portable detection unit 400, whereby the heating temperature of the denaturation phase of the PCR procedure is lessened if necessary to avoid boiling. Thus, the third embodiment provides an added safety feature that is not currently available for conventional portable detection units.

GPS information, such as geographical location, also can be used, either automatically or via user instructions, to make determinations regarding assay parameters, such as temperature, timing, and detection protocols. For example, a first set of assay parameters can be used in a first country and a second set of assay parameters can be used outside another country. It may be desirable to select different detection protocols or parameters based on the laws and regulations that differ by geographic region. By way of example, assay protocol A can be used when in a defined geographic region, but assay protocol B can be used in all other regions. Selection of assay methods and parameters based on geographic regions may be useful for a variety of reasons. For example, different methods or parameters may be required to comply with the laws and regulations in different geographic regions. Selection of different testing methods and parameters based on geographic regions also may be useful to avoid infringing intellectual property rights that exist only in certain jurisdictions. As yet another example, testing methods and parameters may be tailored based on the prevalence of different analytes in different regions. The portable detection unit 400 may be configured to select the testing protocol or parameters based on the data provided by the GPS. In the alternative, the GPS data can be transmitted to a remote server that in turn provides the testing protocol or parameters to the portable detection unit 100 based on the GPS data. In another embodiment, the testing method or parameters are selected based on both the GPS data and information provided by the consumable in the form of memory or a barcode, as discussed above.

In some embodiments, information provided via the consumable can be used to select the testing method, such as, a nucleic acid identification method, a protein identification method, or a combination thereof. Nucleic acid identification methods include, for example, PCR or Linear After the Exponential PCR (LATE-PCR), and reverse transcriptase PCR (RT-PCR). Protein identification methods include, for example, affinity binding-based methods such as antibody-antigen assays.

In a fifth embodiment, the portable detection unit performs one or more assays based on the result of the first assay. The detection unit, either directly or via communication with a remote server, can evaluate the result of a first assay and determine whether or not to perform a second assay and, if a second assay is performed, what type of assay is performed. For example, the portable detection unit can perform an antibody assay that screens for multiple targets, and depending of whether a what target is detected, a subsequent assay, such as PCR, is performed. It also would be possible that further assays would be dictated depending on subsequent results. As another example, the portable detection unit can determine the size or quantity of an analyte in a sample. Based on the size, quantity or type of the analyte, a subsequent test can be performed. The parameters also can be selected based on the results of an earlier test. For example, following an inconclusive assay, parameters may be adjusted in an effort to obtain conclusive results.

The decision as to whether to perform a second test or what second test to perform can be made by the portable detection unit. The decision can be made by the portable detection unit based on software present in unit, for example. The portable detection unit can also transmit data from the first test to a remote server, as discussed above, either alone or in combination with GPS data, and the remote server can specify what, if any, test should be performed next. In this manner, it is the remote server that determines what, if any, subsequent analysis to perform. The portable detection unit can also use the results of a first test in conjunction with information stored on a consumable to determine which, if any, subsequent analysis to perform. For example, a subsequent analysis can be selected based on (a) a failed first analysis (b) using a consumable for the detection of a defined set of analytes. The subsequent analysis can be made using a consumable for the detection of second set of defined analytes.

While the fourth embodiment has been described primarily as it relates to PCR analysis, the fourth embodiment can be used with any assay. For example, the fourth embodiment can be used with mass spectroscopy, IMS, or binding affinity-based techniques, such as antibody binding. A difference in altitude can affect tests that rely on any parameter dependent on altitude, such as atmospheric pressure or melting and boiling points. Moreover, different geographic regions may call for different methods or parameters for reasons completely independent of altitude, as discussed above.

Figure 5:
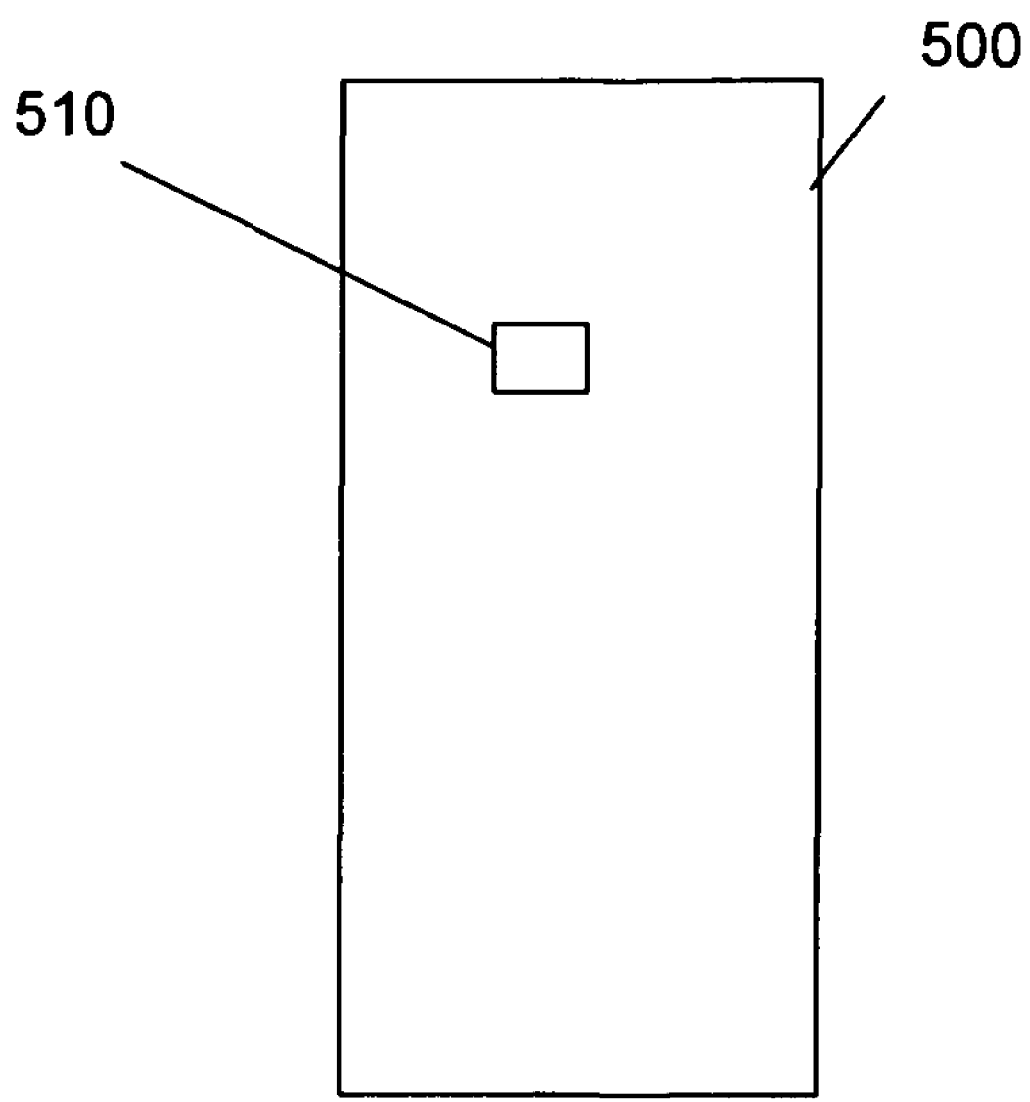
FIG. 5 is a diagram showing a canister containing a consumable that can be utilized in any of the embodiments of the invention.

FIG. 5 shows a canister 500 having a chip 510 provided on an exterior surface thereof, in accordance with the first through fourth embodiments of the invention. In another possible implementation, there are two chips provided at opposite positions on the canister 500, so that the antenna 315 (see FIG. 3) can detect the RF ID chip no matter the disposition of the canister 500 within the usage tray 305 of the portable detection unit. The chip 510 is preferably fixedly attached to the exterior surface of the canister 500, such as by screwing it in place, welding it in place, or gluing it in place.

The embodiments described above have been set forth herein for the purpose of illustration. This description, however, should not be deemed to be a limitation on the scope of the invention. Various modifications, adaptations, and alternatives may occur to one skilled in the art without departing from the claimed inventive concept. For example, sample preparation parameters, as well as PCR parameters, may be provided to the portable detection unit from a remote server. For example, a consumable may incubate a sample in a particular buffer for five minutes, then perform some operations, and then incubate the sample for a further five minutes. Based on that, the remote sensor will provide optimal parameters for going forward with an assay to be performed by the portable detection unit. Also, with respect to the third embodiment and with use of a temperature sensor, it is possible to adjust consumable incubation times to account for a lower operating temperature (as incubation times are related to operating temperature). Still further, changing the cycling parameters may have an affect on the analysis parameters to be used for running an assay, and vice versa, whereby the appropriate cycling parameters and analysis parameters will be provided to a portable detection unit from a remote sensor accordingly. The spirit and scope of the invention are indicated by the following claims.

What is claimed is:

1. A system for testing an unknown sample, comprising: a portable detection unit having stored therein assay parameter information for testing the unknown sample with respect to a plurality of assays; and a remote server providing updated assay parameter information to the portable detection unit; wherein the portable detection unit comprises a wireless transceiver for wireless communicating with the remote server and a means for notifying the remote server whenever the portable detection unit is turned on; and wherein the remote server comprises: means for determining whether or not current assay parameter information stored therein is different from the assay parameter information stored at the portable detection unit, and for outputting the current assay parameter information to the portable detection unit if there is a difference.

2. The system according to claim 1, further comprising a consumable, wherein the assay parameter information stored on the portable detection unit comprises data specific to a reaction on the consumable.

3. The system according to claim 2, wherein the consumable comprises a memory or a barcode.

4. The system according to claim 3, wherein the memory is an RF ID chip.

5. The system according to claim 3, wherein the portable detection unit can read information stored on the consumable.

6. The system according to claim 2, wherein the consumable is a PCR consumable.

7. The system according to claim 6, wherein the PCR consumable identifies the reagents to use, the number of cycles, the time of each cycle, the temperature for each cycle, temperature profiles, detection temperatures, and/or detection excitation and emission wavelengths.

8. The system according to claim 2, wherein the consumable is removable.

9. The system according to claim 1, further comprising a global positioning device.

10. The system according to claim 1, wherein said system can perform at least two assays for testing a sample, wherein the at least two assays can be of the same assay type or different assay types.

11. The system according to claim 10, wherein the assays comprise PCR.

12. The system according to claim 11, wherein the assays comprise a binding affinity-based assay.

13. The system according to claim 12, wherein the binding affinity-based assay is an antibody binding assay.

14. The system according to claim 10, wherein the assays comprise a first assay and a second assay, wherein the first assay comprises a binding affinity-based assay and wherein the second assay comprises a PCR assay.

15. The system according to claim 10, wherein the assays are of the same type.

16. The system according to claim 10, wherein a result from a first assay is used to determine an assay type of a second assay.

17. A method of testing an unknown sample, comprising: storing, at a portable detection unit, assay parameter information for testing the unknown sample with respect to a plurality of assays; wirelessly communicating updated assay parameter information from the remote server to the portable detection unit; notifying, by the portable detection unit, the remote server whenever the portable detection unit is turned on; and determining, by the remote server, whether or not current assay parameter information stored therein is different from the assay parameter information stored at the portable detection unit, and outputting the current assay parameter information to the portable detection unit if there is a difference.

18. A system for testing an unknown sample, comprising: a portable detection unit having stored therein assay parameter information for testing the unknown sample with respect to a plurality of assays; and a remote server providing updated assay parameter information to the portable detection unit, wherein the assay parameter information includes a minimum melt temperature for each of the plurality of assays; an altitude determining unit configured to determine a current altitude of the portable detection unit with respect to sea level; and a melting temperature recalculating unit configured to recalculate the melt temperature for the plurality of assays based on the current height of the portable detection unit.

19. The system according to claim 18, further comprising a prevention unit configured to prevent a particular assay from being run using the portable detection unit, when the recalculated melt temperature is determined to be higher than the minimum melt temperature for the particular assay.

20. The system according to claim 19, wherein prevention unit outputs at least one of an audible or textual warning on a display of the portable detection unit, to inform a user of the prevention of running the particular assay.

21. The system according to claim 18, further comprising a prevention unit configured to prevent a particular assay from being run using the portable detection unit, based on predetermined criteria.

* * * * *